(12) United States Patent
Tu et al.

(10) Patent No.: US 6,238,390 B1
(45) Date of Patent: May 29, 2001

(54) ABLATION CATHETER SYSTEM HAVING LINEAR LESION CAPABILITIES

(75) Inventors: Hosheng Tu; Cary Hata, both of Tustin, CA (US)

(73) Assignee: Irvine Biomedical, Inc., Irvine, CA (US)

(*) Notice: Subject to any disclaimer, the term of this patent is extended or adjusted under 35 U.S.C. 154(b) by 0 days.

(21) Appl. No.: 09/085,543

(22) Filed: May 27, 1998

(51) Int. Cl.$^7$ .................................................. A61B 17/39
(52) U.S. Cl. ................................ 606/41; 606/45; 606/101
(58) Field of Search .......................... 606/41, 42, 45–50; 607/100, 101, 102

(56) References Cited

U.S. PATENT DOCUMENTS

| | | | |
|---|---|---|---|
| 5,354,296 | * | 10/1994 | Turkel ........................................ 606/41 |
| 5,395,363 | * | 3/1995 | Billings et al. .............................. 606/41 |
| 5,634,924 | * | 6/1997 | Turkel et al. ................................ 606/46 |
| 5,766,215 | * | 6/1998 | Muri et al. .................................. 606/46 |
| 5,843,019 | * | 12/1998 | Eggers et al. ............................... 604/22 |
| 5,893,884 | * | 4/1999 | Tu ............................................. 607/120 |

* cited by examiner

*Primary Examiner*—Michael Peffley

(57) ABSTRACT

An improved catheter system having a rollable electrode at its tip section capable of treating a tissue of a patient. A catheter suitable for radiofrequency ablation of cardiac tissues comprises a catheter shaft having a distal section with an open groove, a distal end, a proximal end and at least one lumen extending therebetween, wherein a rollable electrode secured onto a moving wire is disposed at the tip section of the said catheter to treat the tissue. In one embodiment, the rollable electrode is moved forward and/or backward while the RF energy is delivered through the rollable electrode to the tissue, creating a true linear lesion without dragging the catheter.

20 Claims, 6 Drawing Sheets

ABLATION CATHETER SYSTEM HAVING LINEAR LESION CAPABILITIES

FIELD OF THE INVENTION

The present invention generally relates to improved constructions for a catheter system. More particularly, this invention relates to a catheter system and methods for ablating tissues via a steerable ablation catheter comprising a rollable electrode at its tip section, which has linear lesion capabilities.

BACKGROUND OF THE INVENTION

The heart includes a number of normal pathways that are responsible for the propagation of electrical signals from the upper to lower chambers necessary for performing normal systole and diastole function. The presence of an arrhythmogenic site or accessory pathway can bypass or short circuit the normal pathway, potentially resulting in very rapid heart contractions, referred to here as tachycardias.

A variety of approaches, including drugs, implantable pacemakers/defibrillators, surgery, and catheter ablation have been proposed to treat tachycardias. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a physician to accurately steer the catheter to the exact site for ablation. Once at the site, it is important for a physician to control the emission of energy to ablate the tissue within the heart.

Of particular interest to the present invention are radiofrequency (RF) ablation protocols that have been proven to be highly effective in tachycardia treatment while exposing a patient to minimal side effects and risks. Radiofrequency catheter ablation is generally performed after conducting an initial mapping study where the locations of the arrhythmogenic site and/or accessory pathway are determined. After a mapping study, an ablation catheter is usually introduced to the target heart chamber and is manipulated so that the ablations tip electrode lies exactly at the target tissue site. Radiofrequency energy or other suitable energy is then applied through the tip electrode to the cardiac tissue in order to ablate the tissue of the arrhythmogenic site or the accessory pathway. By successfully destroying that tissue, the abnormal signal patterns responsible for the tachycardia may be eliminated. However, in the case of atrial fibrillation (AFib) or atrial flutter, multiple arrhythmogenic sites and/or multiple accessory pathways exist. The conventional catheter with a single "stationary" ablation electrode can not effectively cure the symptoms.

Atrial fibrillation is believed to be the result of the simultaneous occurrence of multiple wavelets of functional re-entry of electrical impulses within the atria, resulting in a condition in which the transmission of electrical activity becomes so disorganized that the atria contracts irregularly. Once considered a benign disorder, AFib now is widely recognized as the cause of significant morbidity and mortality. The most dangerous outcome from AFib is thromboembolism and stroke risk, the latter due to the chaotic contractions of the atria causing blood to pool. This in turn can lead to clot formation and the potential for an embolic stroke. According to data from the American Heart Association, about 75,000 strokes per year are AFib-related.

The tip section of a conventional electrophysiology catheter that is deflectable usually contains one large electrode about 4 to 8 mm in length for ablation purposes. Sometimes, a plurality of long electrodes is used in creating a contiguous linear lesion. The lesion is generally not deep because of potential impedance rise of the tissue in contact with the "stationary" catheter electrode(s) and thereafter the ablation time needs to be cut short. The word "stationary" means that the contact point of the electrode with the tissue is the same point unless the electrode is rollable or rotatable so that the contact point changes from time to time.

In some cases, the contact of a stationary electrode of the conventional catheter with tissues reportedly results in potential tissue adhering to the electrode. A rollable electrode on a stationary catheter is in need to reduce the tissue contact impedance rise and temperature rise by slightly moving the rollable electrode back and forth so that the temperature rise is decreased by the surrounding fluid or by the irrigation fluid.

However, the conventional catheter simulating the "rollable electrode" phenomenon by dragging the catheter back and forth has one big drawback. By moving the tip section of the catheter back and forth, the target tissue site may get lost. Therefore, it is imperative to the keep the catheter stationary while creating a real linear lesion, not a contiguous linear lesion for atrial flutter or atrial fibrillation indications.

Avitall in the U.S. Pat No. 5,242,441, teaches a rotatable tip electrode. Said electrode is secured to a high torque wire for rotation and electrical conductivity. The tissue contact site is always the same spot even the electrode is rotated. Moreover, a movable band electrode has been recently introduced to the market to simulate the "rollable electrode" concept. Since the said band electrode does not roll, the contact surface spot of the said band electrode with tissues is always the same spot. The potential coagulum at the contact electrode surface spot due to impedance and temperature rises, would not go away because of its relatively stationary position of the rotatable tip electrode or the movable band electrode.

While a radiofrequency electrophysiology ablation procedure using an existing catheter has had promising results, the tip section of a known catheter usually has a fixed non-rollable electrode when contacting the tissue for ablation purposes. Therefore there is a need for an improved catheter and methods for making a deeper and larger lesion in the cardiac tissue employing a rollable electrode means on a "stationary" catheter during ablation procedures.

SUMMARY OF THE INVENTION

In general, it is an object of the present invention to provide a rollable electrode to a catheter. The "rollable electrode" is defined in this invention as the electrode that is rollable in the axial direction with respect to the catheter shaft itself. The rollable electrode is different from the slidable electrode, in which the contact point of a slidable electrode with the tissue is almost at the same point. A ball-type rotatable electrode, which is disclosed in patent application Ser. No. 08/867,469, filed Jun. 2, 1997, now U.S. Pat. No. 5,843,152, is cited here as reference.

It is another object to provide at least one rollable electrode to at least one catheter sub-shaft of a catheter probe, such as a basket catheter or multiple-loop electrode.

It is still another object to provide fluid infusion and irrigation to the rollable electrode portion of a catheter of the present invention. This capability of fluid infusion/irrigation may be applicable to the drug delivery means for treating tumors or cancers. The capability of fluid infusion and irrigation may be applicable to special means of cooling off the tissue contact site due to impedance rise as a result of ablation operation.

It is another object of the invention to provide an ablation catheter with a tip section having a rollable electrode, wherein the freely rollable electrode in the distal tip section of a catheter to be used in effectively treating the tissue of a patient. This catheter is particularly useful for treating the patient with tachycardia as a result of its cooled electrode by heat dissipation to the surrounding environment. The fluid may be selected from the group consisting of cold saline, saline, heparin, antibiotics, chemotherapy and therapeutics fluids.

In one embodiment, an ablation catheter system comprises a catheter shaft having a distal tip section, a distal end, a proximal end, and at least one lumen extending therebetween, wherein the distal tip section has an open groove. A handle is attached to the proximal end of the catheter shaft, wherein an electrode rolling controller having a moving wire is located within the handle, wherein the moving wire is capable of being moved forward and backward by the electrode rolling controller. An electrode element means consists of a rollable electrode, a support, and an anchoring leg means disposed inside the open groove, wherein the rollable electrode is positioned on the support and wherein the support is connected to the anchoring leg means which is then secured onto the moving wire. In another embodiment, the rollable electrode of the present invention is free to roll when the moving wire is caused to move forward or backward. The moving wire is also used as the conducting wire, which is connected to one contact pin of the connector that is secured at the proximal end of the handle. Therefrom, the conducting wire is connected to an external RF generator for delivery of RF energy to the rollable electrode during ablation operations and/or to an EKG monitor for recording and displaying of the endocardial or electrical signal measured by the rollable electrode. The moving wire and the electrode element are made of insulated conductive material.

A fluid source is positioned at one end of the catheter for supplying a fluid flow through the lumen of the said catheter shaft to the tip section that has a rollable electrode. Therefore at ablation time, the tip section with a rollable electrode is positioned against the tissues to be ablated. The fluid is continuously or intermittently supplied through the lumen to evenly cover and rinse the electrode so that the impedance rise at the contact site is substantially reduced. Cooling off the electrode during RF energy delivery will result in optimal ablation efficiency and a desired deep and large lesion. The fluid can also be used to therapeutically treat the tissues.

The ablation catheter further comprises a steering mechanism at the handle for controlling the deflection of the said distal tip section having a rollable electrode. Usually a rotating ring or a push-pull plunger is employed in the steering mechanism. In another embodiment, the steerable ablation catheter comprises a bidirectional deflection or multiple curves deflection of the tip section. One end of the steering wire is attached at certain point of the tip section of the said catheter shaft. The other end is attached to the steering mechanism at the handle. The steering mechanism on a steerable catheter or device is well known to those who are skilled in the art.

A fluid conveying lumen is associated with the elongate catheter shaft, and is preferably disposed within the catheter shaft along the longitudinal axis thereof. The lumen is adapted to communicate with a fluid supply source to convey fluid from the source and through the lumen to be discharged out of the tip section containing a rollable electrode.

The invention also comprises a method and system for controlling the flow rate of fluid through the lumen to optimize the cooling effect of the energy-delivering electrode of the catheter. The control system preferably regulates the flow rate based on signals representative of the temperature of the catheter tip and/or tissue impedance.

In a particular embodiment, at least one other electrode is disposed at the tip section of the catheter shaft. One conducting wire which is soldered to the said electrode passes through the lumen of the catheter shaft and the interior void of the handle and is thereafter soldered to a contact pin of the connector secured at the proximal end of the handle. Therefrom, the conducting wire is connected to an external RF generator for delivery of RF energy during ablation operations and/or to an EKG monitor for recording and displaying of the endocardial or epicardial electrical signal from the electrode.

In an additional embodiment, the ablation system further comprises a temperature sensing and close-loop temperature control mechanism for the electrode having at least one temperature sensor at the tissue contact site of the electrode. The location of the temperature sensor is preferably in the very proximity of one of the electrodes. In a still further embodiment, a method for operating an ablation catheter further comprises a programmed temperature control mechanism for independently controlling the delivery of RF energy of each electrode of the ablation catheter.

In one embodiment, the material for the electrodes may consist of conductive metals such as platinum, iridium, gold, silver, stainless steel, Nitinol, or an alloy of their mixture.

A method for operating an ablation catheter system having a rollable electrode of the present invention at the distal tip section contacts the interior wall within a heart chamber. The method comprises percutaneously introducing the catheter system through a blood vessel to the heart chamber, wherein the distal tip section comprises a rollable electrode. The distal tip section of the catheter shaft is positioned on the interior wall of the heart chamber. Then the rollable electrode is moved forward and/or backward by steering the moving wire from the electrode-rolling controller on the handle, while simultaneously applying RF energy to the rollable electrode through the moving wire for tissue ablation.

The catheter system of the present invention has several significant advantages over known catheters or ablation techniques. In particular, the rollable electrode of a steerable ablation catheter of this invention may result in a real linear lesion that is highly desirable in atrial flutter and atrial fibrillation treatments.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

Figure 1:
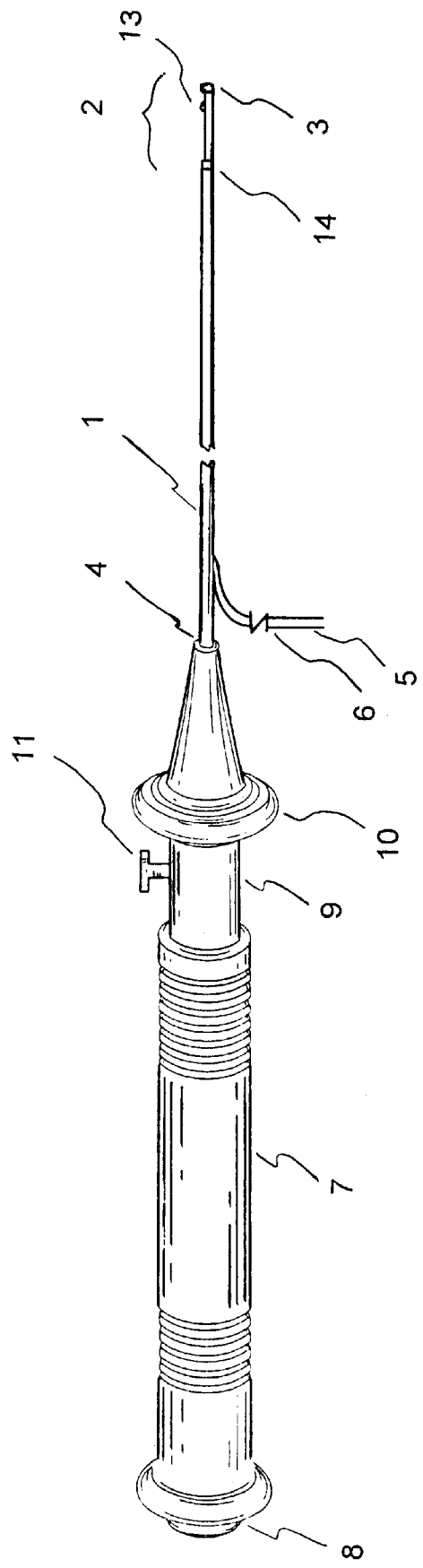
FIG. 1 is an overall view of a catheter system having a rollable electrode means at its distal tip section constructed in accordance with the principles of the present invention.

FIG. 1 shows an overall view of the catheter system having a rollable electrode at its distal tip section. A catheter system constructed in accordance with the principles of the present invention comprises: a catheter shaft 1 having a distal tip section 2, a distal end 3, a proximal end 4, and at least one lumen extending therebetween. The catheter system comprises a fluid infusion mechanism 5 close to the proximal end 4 of the catheter shaft 1. A control valve 6 is provided to the fluid infusion mechanism 5 which is externally connected to a fluid supply source having a pump and means (not shown) for controlling the flow rate of fluid through the lumen to optimize the cooling of the electrode of the catheter. A handle 7 is attached to the proximal end 4 of the said catheter shaft 1.

A connector 8 secured at the proximal end of the catheter system, is part of the handle section 7. The handle has one optional steering mechanism 9. The steering mechanism 9 is to deflect the tip section 2 of the catheter shaft 1 for catheter maneuvering and positioning. By pushing forward the front plunger 10 of the handle 7, the distal tip section 2 of the catheter shaft deflects to one direction. By pulling back the front plunger 10, the tip section returns to its neutral position. In another embodiment, the steering mechanism 9 at the handle 7 comprises means for providing a plurality of deflectable curves on the distal tip section 2 of the catheter shaft. The mechanism of an ablation catheter having multiple flexible curves is described by a patent application Ser. No. 08/763,614, filed Dec. 11, 1996, now U.S. Pat. No. 5,782,828.

The catheter system has an electrode rolling controller 11 on the handle 7, wherein a moving wire 12 (shown in FIG. 3) is secured to the electrode rolling controller and is capable of moving forward and backward as controlled by the electrode rolling controller 11. A rollable electrode 13 is disposed and secured on the moving wire 12 so that the rollable electrode is controlled back and forth by the said electrode-rolling controller 11. The rolling range of the rollable electrode 13 at the distal tip section 2 is restricted by a first stopper 14 and a second stopper 15.

Figure 2:
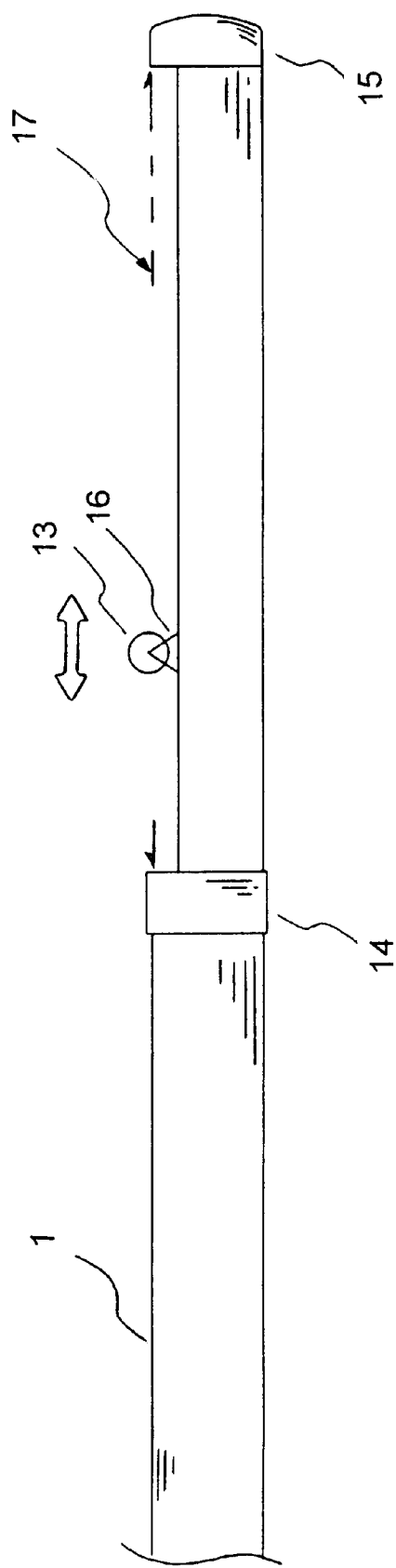
FIG. 2 is a close-up view of the distal section of the catheter system comprising a rollable electrode means at the distal end having linear lesion capabilities.

FIG. 2 shows a close-up view of the distal section 2 of the catheter system comprising a rollable electrode 13 at the distal portion. The rollable electrode 13 and its support 16 sits on a moving wire 12. The traveling action of the rollable electrode 13 within the open groove 17 is controlled by the electrode rolling controller 11 while the traveling range is restricted by the first stopper 14 and the second stopper 15.

Figure 3:
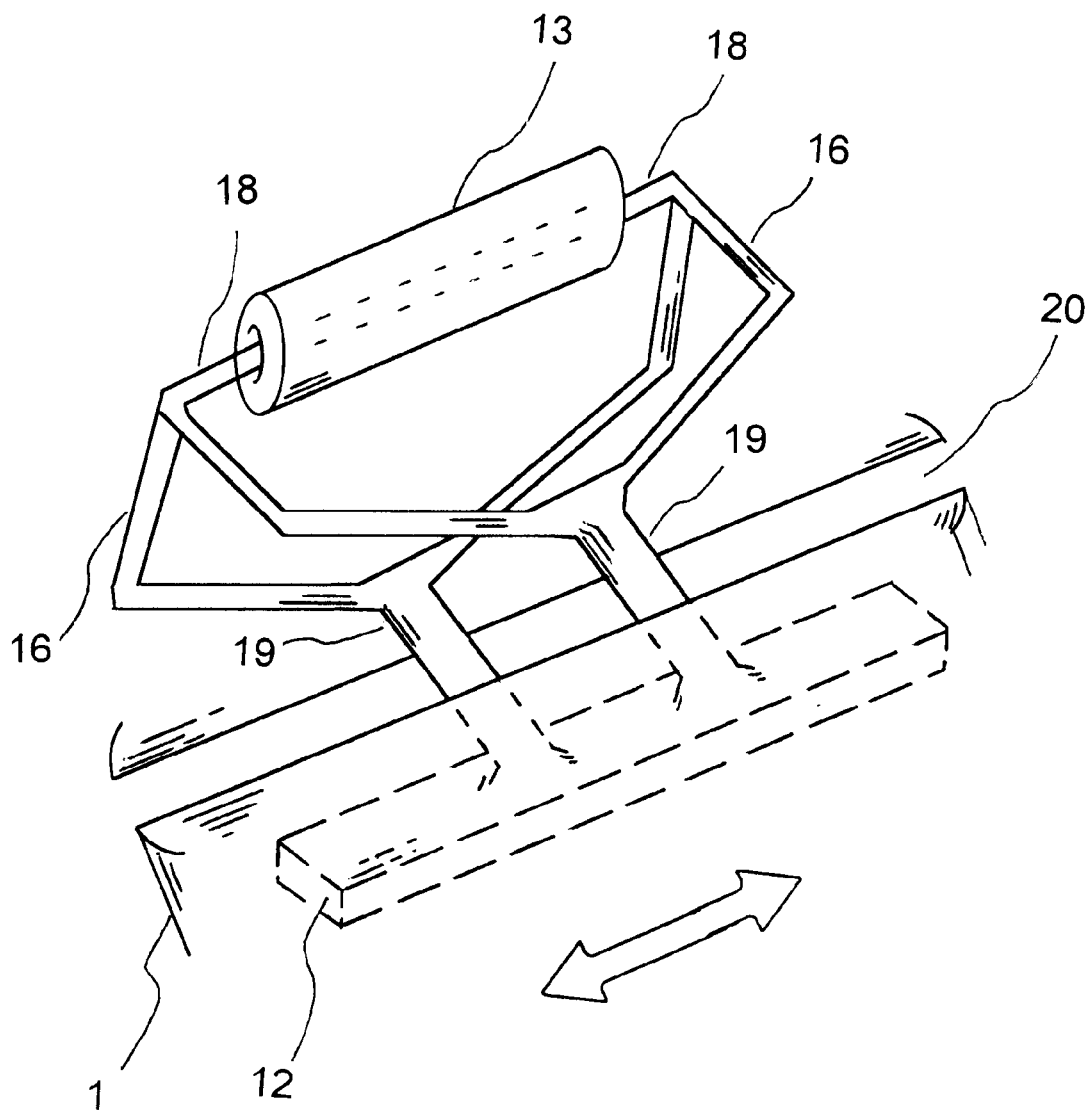
FIG. 3 is a perspective view of the electrode element, including a rollable electrode at the distal section of a catheter system.

FIG. 3 shows a perspective view of the electrode element, including a rollable electrode 13 at the distal section 2 of a catheter system. The electrode element is consisted of a rollable electrode 13, a pair of electrode shafts 18, a plurality of supports 16, and an anchoring leg means 19. The rollable electrode can be selected from a group consisting of a cylindrical roller, a ball-type roller, an oval-type roller, a porous roller, a roller with studded surface and the like. The electrode element is preferably made of conductive material, while the surfaces of the shafts 18, supports 16, the anchoring leg means 19, and the moving wire 12 are preferably covered with an insulating material or insulated. The anchoring leg means 19 is secured to the moving wire 12 through an open slit 20 of the open groove 17, wherein the moving wire 12 is preferred to be made of a flat wire. When the moving wire is pushed forward by the electrode rolling controller 11, the rollable electrode 13 moves forward, too. The rollable electrode 13 tends to roll when it contacts the tissues.

In one embodiment, a fluid conveying lumen 21 is associated with the elongate catheter shaft 1, and is preferably disposed within the catheter shaft along the longitudinal axis thereof. The fluid conveying lumen is adapted to communicate with a fluid supply source (not shown) to convey fluid from the source and through the said lumen to be discharged out of the tip section 2 at the slit opening 20. The fluid flow rate from the fluid infusion mechanism 5 may be between approximately 5 ml/min to 20 ml/min. In another embodiment, the tip section 2 of the catheter shaft 1 comprises at least one other electrode 22. The stopper 14 or 15 may be considered as one of the at least one other electrode 22. The electrodes are formed of conducting materials selected from the group of platinum, iridium, gold, silver, stainless steel, and Nitinol.

Figure 4:
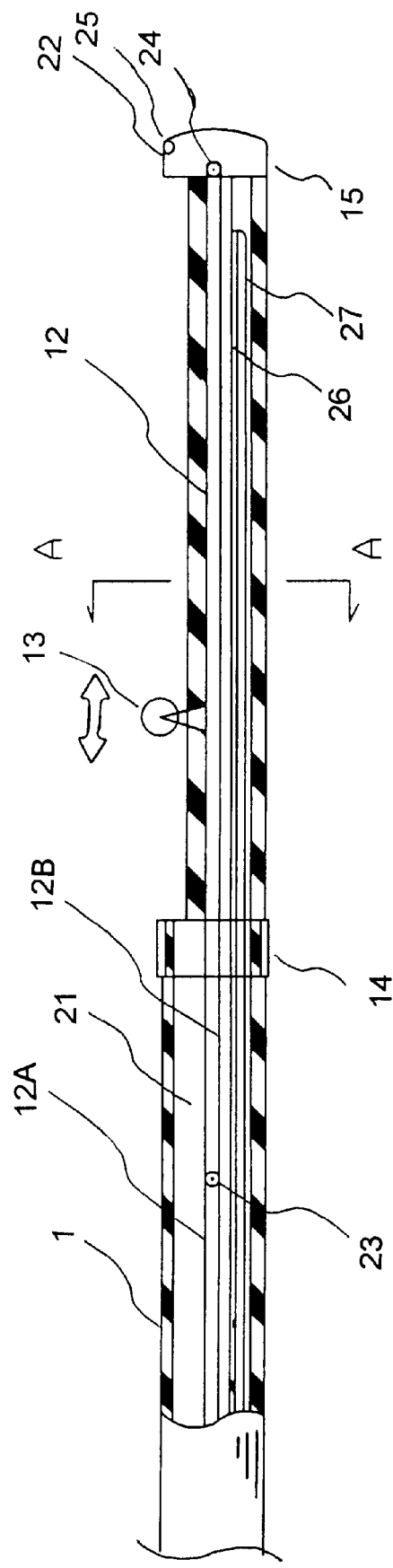
FIG. 4 is a cross-sectional view of the distal section of a catheter system comprising a rollable electrode and its moving wire configuration.

FIG. 4 shows a cross-sectional view of the distal section 2 of a catheter system comprising a rollable electrode 13 and its moving wire configuration 12. The electrode rolling controller 11 and its associated moving wire 12 constitute the main mechanism of the electrode rolling capabilities. In one embodiment, the moving wire 12 is a close loop wiring and comprises a upper wire 12A and a lower wire 12B, which are supported by a first pulley 23 near the distal portion of the catheter shaft 1 and a second pulley 24 near the distal end of the catheter shaft 1. The electrode element, including a rollable electrode 13, a pair of electrode shafts 18, a plurality of supports 16, and anchoring leg means 19 are secured on the moving wire 12.

The at least one electrode 22 has an insulated conducting wire (not shown) secured to the electrode, which passes through the lumen of the catheter shaft 1 and is soldered to a contact pin of the connector 8 at the proximal end of the handle 7. The conducting wire from the end of the connector is externally connected to an EKG monitor for diagnosis or to a RF generator during an electrophysiology ablation procedure. Therefrom, the RF energy is transmitted through the conducting wire to the electrode and the RF energy is delivered to the target tissue.

A temperature sensor 25, either a thermocouple means or a thermister means, is constructed at the proximity of the electrode 13 or 22 to measure the tissue contact temperature when RF energy is delivered. The temperature sensing wire (not shown) from the thermocouple or thermister is connected to one of the contact pins (not shown) of the connector 8 and externally connected to a transducer and to a temperature controller. The temperature reading is thereafter relayed to a close-loop control mechanism to adjust the RF energy output. The RF energy delivered is thus controlled by the temperature sensor reading or by a pre-programmed control algorithm.

In one embodiment, the catheter of this invention is meant to provide fluid communication and commensurate flow of fluid originating inside the tip section of the catheter shaft to the electrode exterior surface, which directs the fluid flow from inside the catheter shaft over the exterior surface of the electrode to provide a fluid protective layer surrounding the electrode to minimize temperature elevation of the electrode with biological tissues. This fluid protective layer surrounding the rollable electrode is better maintained when the electrode is freely rollable.

The ablation catheter system further comprises a steering mechanism 9 at the handle 7 for controlling the deflection of the said distal tip section 2 having a rollable electrode 13. Usually a rotating ring or a push-pull plunger 8 is employed in the steering mechanism. A flat wire 26 is disposed at the distal tip section 2. A pulling wire 27 is used to control the degree of pulling on the flat wire 26, thus effects the deflection of the catheter shaft 1 at the distal portion 2.

Figure 5:
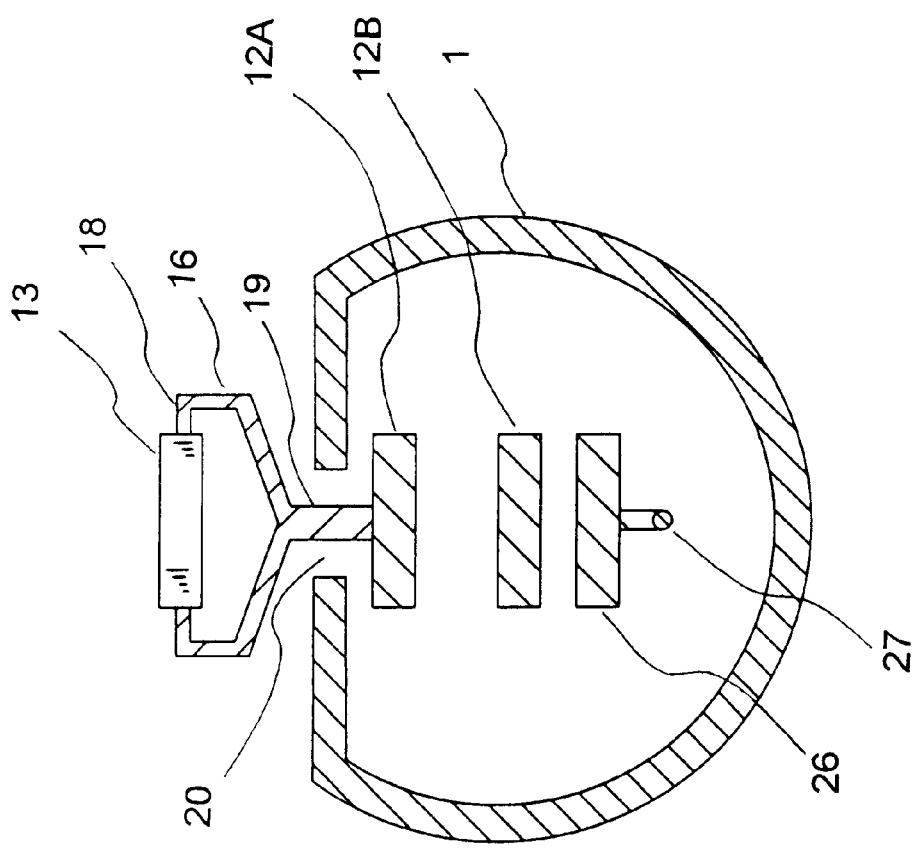
FIG. 5 is a transverse view of the attachment setup of the rollable electrode on a moving wire inside the open groove of a catheter shaft.

FIG. 5 shows a transverse view of the attachment setup of the rollable electrode on a moving wire 12 inside the open groove 17 of a catheter shaft 1. The electrode element comprises a rollable electrode 13, electrode shafts 18, supports 16, and anchoring leg means 19. The anchoring leg means 19 is firmly secured on the upper moving wire 12A. The upper moving wire 12A and the returning lower moving wire 12B constitute a close-loop wiring, which is controlled by the electrode rolling controller 11 for moving the said wire forward or backward.

Figure 6:
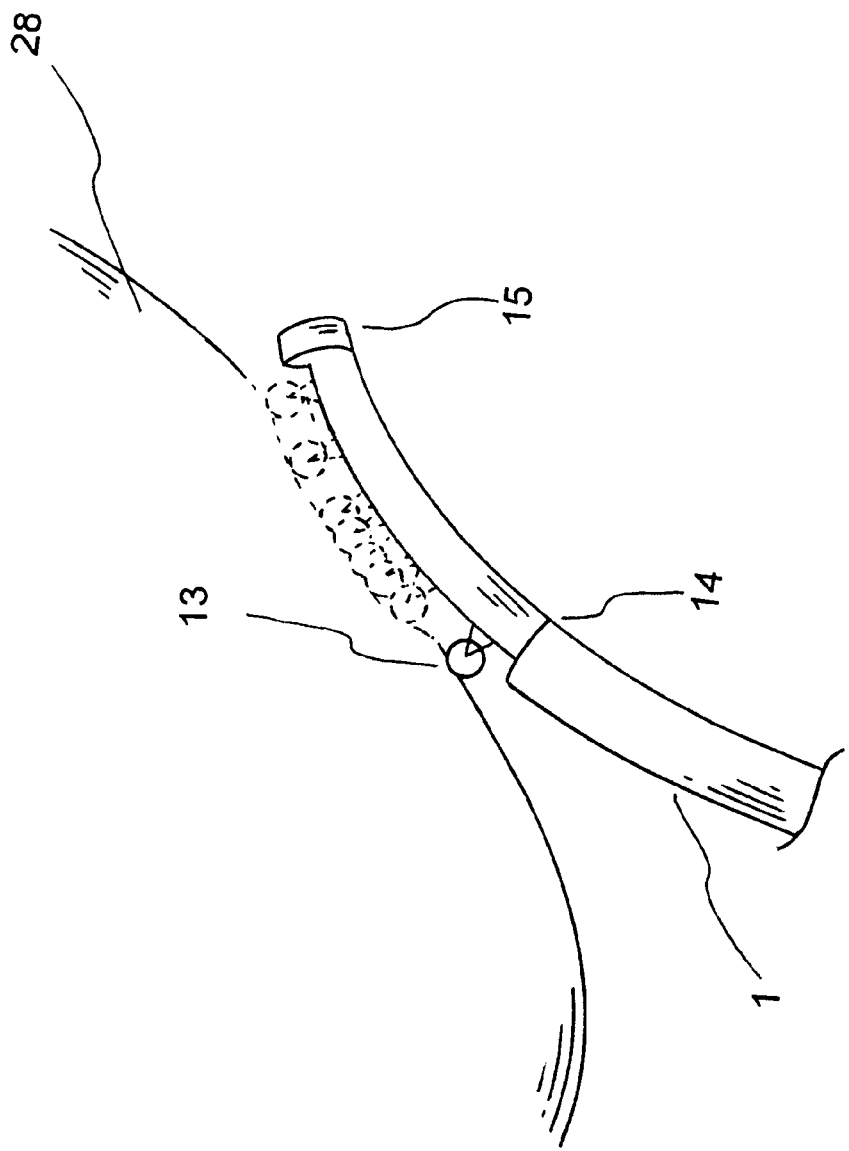
FIG. 6 is a simulated view of the catheter of the present invention in contact with the tissues.

FIG. 6 shows a simulated view of the catheter of the present invention in contact with the tissues 28. The rollable electrode 13 moves from the first stopper end 14 to the second stopper end 15 along the open groove 17 of the distal end section 2 of the catheter shaft 1 by manipulating the electrode rolling controller 11 at the handle 7. During moving the electrode 13 forward and/or backward, the catheter itself is stationary with respect to the location of the tissues 28. The RF energy is simultaneously delivered to the tissue to create a "true" linear lesion for tissue ablation.

From the foregoing, it should now be appreciated that an improved catheter system having a rollable electrode and an optional fluid infusion and irrigation capability has been disclosed for ablation procedures, including endocardial, epicardial, or body tissue. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter system comprising:
    a flexible catheter shaft having a distal tip section, a distal end, a proximal end, and at least one lumen extending therebetween, wherein the distal tip section has an elongated open groove;
    a handle attached to the proximal end of the catheter shaft, wherein an electrode rolling controller having a moving wire is located within the handle, wherein the moving wire is capable of being moved forward and backward by the electrode rolling controller; and
    an electrode element comprising a rollable electrode, a support, and an anchoring leg means disposed inside the open groove, wherein the rollable electrode is positioned on the support and wherein the support is connected to the anchoring leg means which is then secured onto the moving wire.

2. The catheter system of claim 1, wherein the moving wire and the electrode element are made of conductive material.

3. The catheter system as in claim 1, further comprising fluid means for providing a fluid to the distal tip section of the catheter shaft and disposed out of the open groove.

4. The catheter system of claim 3, wherein the fluid is selected from the group consisting of saline, heparin, antibiotics, chemotherapy and therapeutic fluids.

5. The catheter system as in claim 4 further comprising a steering mechanism at the handle for controlling the deflection of the distal tip section of the catheter system.

6. The catheter system of claim 5, wherein the steering mechanism provides a plurality of deflectable curves on the distal tip section of the catheter system.

7. The catheter system as in claim 1 further comprising at least one additional electrode disposed at the distal tip section of the catheter shaft.

8. The catheter system as in claim 1 further comprising a RF energy generator, wherein the RF energy is delivered to the rollable electrode of the electrode element.

9. The catheter system as in claim 8, further comprising a temperature sensing means at the distal tip section.

10. The ablation catheter as in claim 1, further comprising a material of the rollable electrode being selected from the group consisting of platinum, iridium, gold, silver, stainless steel, and Nitinol.

11. A method for operating an ablation catheter system having a rollable electrode at the distal tip section contacting the interior wall within a heart chamber, the catheter system comprising: a flexible catheter shaft having a distal tip section, a distal end, a proximal end, and at least one lumen extending therebetween, wherein the distal tip section has an elongated open groove; a handle attached to the proximal end of the catheter shaft, wherein an electrode rolling controller having a moving wire is located within the handle, wherein the moving wire is capable of being moved forward and backward by the electrode rolling controller; and an electrode element having a rollable electrode, a support, and an anchoring leg means disposed inside the open groove, wherein the rollable electrode is positioned on the support and wherein the support is connected to the anchoring leg means which is then secured onto the moving wire;
    the method comprising:
        (a) percutaneously introducing the catheter system through a blood vessel to the heart chamber, wherein the distal tip section comprises a rollable electrode;
        (b) positioning the distal tip section of the catheter shaft on the interior wall of the heart chamber; and
        (c) simultaneously moving the rollable electrode forward and/or backward by steering the moving wire from the electrode-rolling controller on the handle, and applying RF energy to the rollable electrode for tissue ablation.

12. The method for operating an ablation catheter system as in claim 11, the catheter system further comprising fluid being supplied to the distal tip section of the catheter shaft and disposed out of the open groove.

13. The method for operating an ablation catheter system as in claim 11, the catheter system further comprising a steering mechanism at the handle for controlling the deflection of the distal tip section of the catheter system.

14. The method for operating an ablation catheter system as in claim 11, wherein the distal tip section of the catheter system is dragged along the interior wall of the heart chamber.

15. A tissue ablation catheter system comprising:
    a flexible catheter shaft having a distal tip section, a distal end, a proximal end, and at least one lumen extending therebetween, wherein the distal tip section has an elongated open groove;

a handle attached to the proximal end of the catheter shaft, wherein an electrode rolling controller having a moving wire is located within the handle, wherein the moving wire is capable of being moved forward and backward by the electrode rolling controller;

an electrode element having a rollable electrode, a support, and an anchoring leg means disposed inside the open groove, wherein the rollable electrode is positioned on the support and wherein the support is connected to the anchoring leg means which is then secured onto the moving wire; and a RF energy generating means, wherein the RF energy is delivered to the rollable electrode for tissue ablation.

16. The tissue ablation catheter system as in claim 15, further comprising fluid means for providing a fluid to the distal tip section of the catheter shaft and disposed out of the open groove.

17. The tissue ablation catheter system as in claim 15 further comprising a steering mechanism at the handle for controlling the deflection of the distal tip section of the catheter system.

18. The tissue ablation catheter system of claim 17, wherein the steering mechanism provides a plurality of deflectable curves on the distal tip section of the catheter system.

19. The tissue ablation catheter system as in claim 15 further comprising at least one additional electrode disposed at the distal tip section of the catheter shaft.

20. The tissue ablation catheter system as in claim 15, further comprising a temperature sensing means at the distal tip section.

* * * * *